(12) United States Patent
Peng

(10) Patent No.: US 9,446,403 B2
(45) Date of Patent: Sep. 20, 2016

(54) MICRO-CHANNEL CHIP

(71) Applicant: XIAMEN XINCHUANG BIOLOGICAL TECHNOLOGY CO., LTD., Xiamen (CN)

(72) Inventor: Xingyue Peng, Xiamen (CN)

(73) Assignees: XIAMEN XINCHUANG BIOLOGICAL TECHNOLOGY CO., LTD., Xiamen, Fujian (CN); Xingyue Peng, Xiamen, Fujian (CN)

( * ) Notice: Subject to any disclaimer, the term of this patent is extended or adjusted under 35 U.S.C. 154(b) by 91 days.

(21) Appl. No.: 14/353,337

(22) PCT Filed: Oct. 23, 2012

(86) PCT No.: PCT/CN2012/083372
§ 371 (c)(1),
(2) Date: Apr. 22, 2014

(87) PCT Pub. No.: WO2013/060260
PCT Pub. Date: May 2, 2013

(65) Prior Publication Data
US 2014/0273190 A1    Sep. 18, 2014

(30) Foreign Application Priority Data

Oct. 24, 2011   (CN) .................... 2011 2 0407861 U

(51) Int. Cl.
*G01N 33/00*   (2006.01)
*B01L 3/00*    (2006.01)
*G01N 35/10*   (2006.01)

(52) U.S. Cl.
CPC ...... *B01L 3/502707* (2013.01); *B01L 3/50273* (2013.01); *B01L 2300/088* (2013.01); *B01L 2400/0481* (2013.01); *G01N 2035/1044* (2013.01)

(58) Field of Classification Search
CPC ................... B01L 3/502707; B01L 3/50273; B01L 2300/088; G01N 33/00; G01N 3/50273
See application file for complete search history.

(56) References Cited

U.S. PATENT DOCUMENTS

2009/0253181 A1* 10/2009 Vangbo ............ G01N 27/44791
435/91.1

* cited by examiner

*Primary Examiner* — Sam P Siefke

(57) ABSTRACT

A micro-channel chip comprises two gas control channels, a liquid inlet channel, a liquid outlet channel, a piston channel, and a micro pump including two micro-valves and a plurality of micro-channels. One of the gas control channels communicates with one end of the piston channel and communicates with the two micro-valves and the liquid inlet channel respectively via the micro-channels. The other one of the gas control channels communicates with the two micro-valves and the liquid outlet channel respectively via the micro-channels. The other end of the piston channel communicates with one of the micro-valves via the micro-channels.

5 Claims, 14 Drawing Sheets

B

MICRO-CHANNEL CHIP

BACKGROUND OF THE INVENTION

1. Field of the Invention

The present invention relates to a filed of manufacturing micro-channel chips, particularly to the structure and the integration of micro-components of the micro-channel chip system.

2. Description of the Related Art

A micro-channel chip is a main technique for the laboratory on a chip. In the same way as computation chips, the reliable integration is an important part to decide whether the laboratory on a chip can be applied to various laboratory researches and habitual medical inspections, such as life science, chemistry and physics. As the high-scale integrated circuit (IC) benefits from the photoetching technique, so problems of high-scale integrated micro-fluidic circuits (IFC) related to the integration, costs, stability and adaptability can be solved if micro-components of the micro-fluidic circuit, namely micro-channel circuit, are like IC to be formed by photoetching.

SUMMARY OF THE INVENTION

An objective of the present invention is to provide a micro-channel chip which allows multiple micro-components of the micro-channel chip, such as micro-pumps, micro-valves, unicellular or multicelluar experimental units, gas exchange units, to be photoetched and formed at one time and further applies the industrialized printing technique to attain multi-layered and high-integrated micro-channel chips with low cost manufacturing.

To attain the above objective, the present invention provides a solution as follows:

An important dynamic component of a micro-channel chip focuses on a micro-pump integration design, which includes two gas control channels, a liquid inlet channel, a liquid outlet channel, a piston channel, and a micro-pump which includes two micro-valves and a plurality of micro-channels. One of the gas control channels communicates with one end of the piston channel and communicates with the two micro-valves and the liquid inlet channel respectively via the micro-channels. The other one of the gas control channels communicates with the two micro-valves and the liquid outlet channel respectively via the micro-channels. The other end of the piston channel communicates with one of the micro-valves via the micro-channels.

The micro-channels are gradually narrowed.

The micro-pump is characterized in that such structure can be designed within an area of one square millimeter on the chip and can be designed into a smaller dimension according to demand to attain the high density of integration.

The micro-pump is characterized in that the digital gas pressure operated by a driving pump can be controlled to lessen from three channels to two channels, thereby simplifying the order sequence of control signals.

The micro-pump is characterized in that such structure possesses a high fault-tolerant recovery function, which does not need to be pre-input at time of initialization and attains a strong capability of resisting the bubble block while operating. The restoring procedure of the pump is effective and easy to operate.

The micro-pump is characterized in that such design is a single-layered geometrical space structure on the planar surface and is extraneous to the physical material of the chip. The adoption of other materials like plastic materials which are likely to be manufactured in industrialization (printing manufacture) as the chip basic material does not affect the achievement of its functions. Therefore, the structure can be applied to the chip with other materials, such as glass, silicon sheets, and composite materials like plastic materials.

The aforesaid features of the micro-pump design allow the design to be compatible with multiple micro-components formed by photoetching, such as micro-pumps, micro-valves, unicellular or multicelluar experimental units, and gas exchange units and to attain an integration of the multi-functional chip on a designed planar surface via an integrated design.

The aforesaid integrated chips on the planar surface can be connected with each other through a middle chip with holes in order to develop the design of integration or other functions on a direction of the normal line (the third dimension) of the planar surface of the chip.

The aforesaid single-layered design can be directly applied to industrialized printing production. By the middle layer with holes, the multi-layered high-scale integrated chips can be made. The multi-layered chips can be industrially printed in amass production as well.

According to the above structure, the new micro-pump of the micro-channel chip and the aforesaid micro-components can execute a single-layered or multi-layered high-density integration on hard materials, such as glass and silicon sheets, and can also set at a high-density integration on other elastic materials like plastic materials and execute a printing production, thereby fulfilling the high-scale integrated micro-channel chip with industrialization and low cost manufacturing.

DETAILED DESCRIPTION OF THE PREFERRED EMBODIMENTS

1. The Integration Design of the Micro-Pump

Figure 1A:
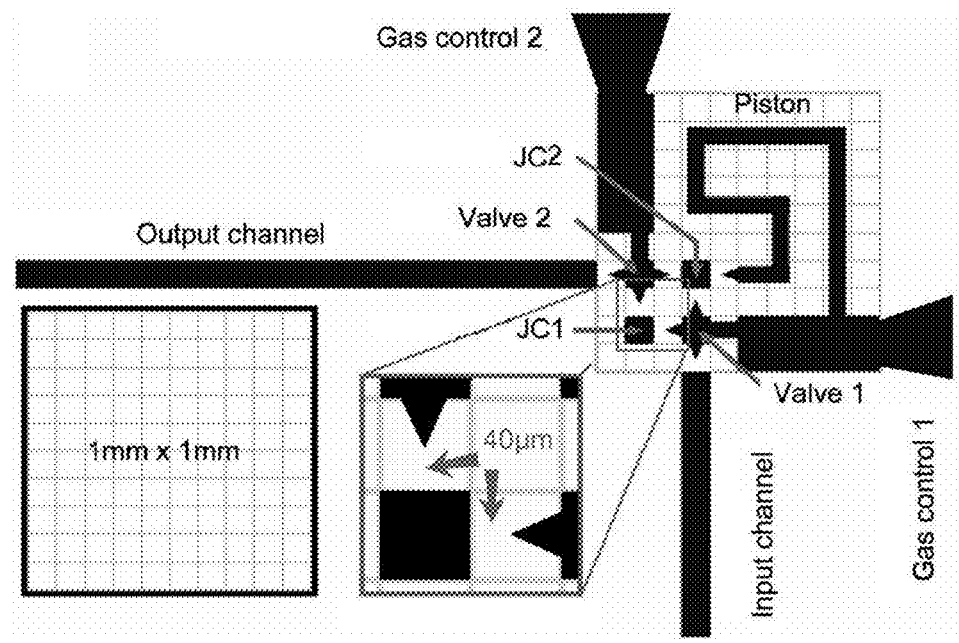
FIGS. 1a-1c are schematic views showing a designed micro-pump within one square millimeter, and the micro-pump is formed by one-time glass etching. The black area of the mask design (a) shows the etching area, and the blue grid in the figure shows the area of one square millimeter (the side length of the small grid is 100 millimeters); (b) shows the situation after the one-time glass etching; and (c) shows that the micro-fluid (orange) is pushed by the pump and goes from the lower vertical channel pump to the left horizontal channel while operating.

Referring to FIG. 1*a*, in order to design the micro-pump into a micro-component which is smaller, more stable to operation and easier to attain the high integration, the present invention has the following features: A. The integral design is disposed within a square area of 1 mm$^2$ to facilitate an easy arrangement in the design, and the dimension can reach the standard of integration smaller than the millimeter; B. the piston and the inlet valve (valve 1) are integrated to allow the inlet valve and the piston to use the same gas pressure signal, thereby decreasing the burden of the control signal and further lessening the space where the design occupies; C. Two square channels (JC1,JC2) of 100 millimeters are adopted between every channel for connecting, and such channel having the aspect ratio (length-width ratio) of 1:1 can simplify the structure and make the operation more reliable to facilitate the fault treatment and restoring step, whereby the design itself increases the capability of resisting the bubble block as well.

Figure 1B:
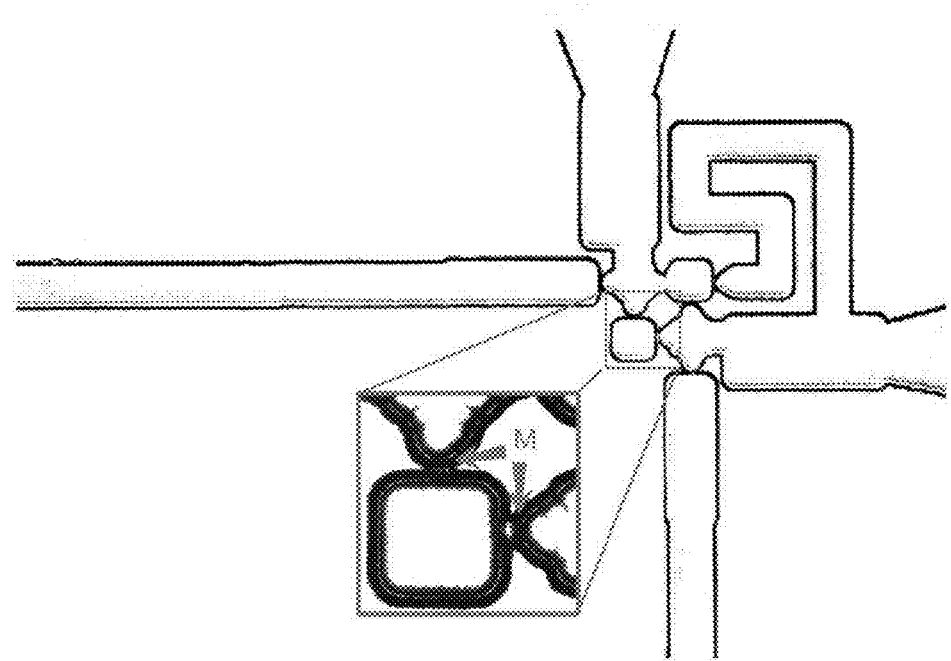
Figure 1C:
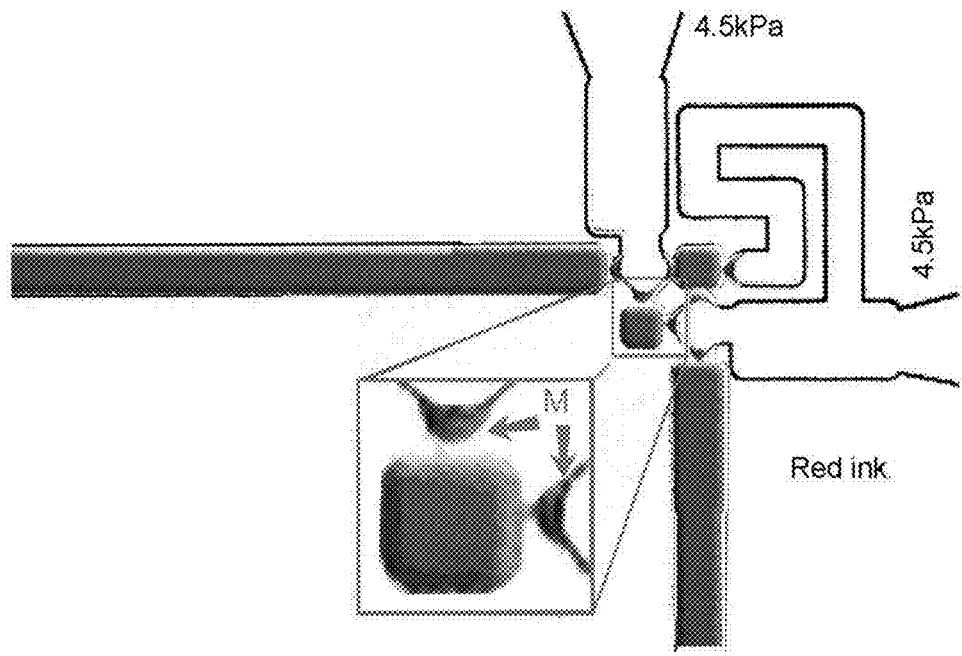
Figure 2A:
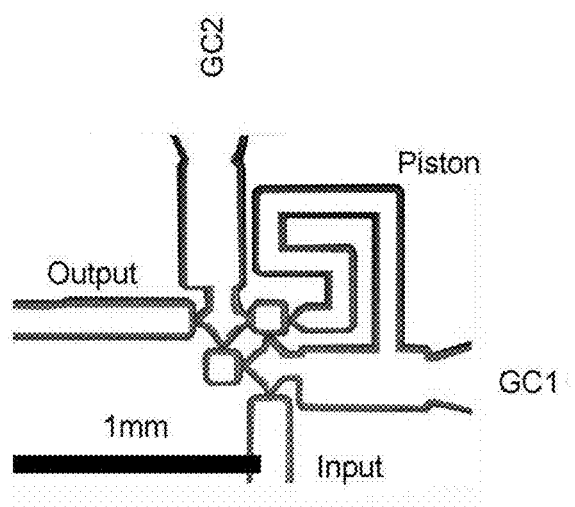
FIGS. 2a-2d are schematic views showing the initialization of the pump. The liquid in the empty micro-channel system (a) can enter (shown in the red mark in (b)) from the inlet passage (the input channel in a lower place of the figure); the redundant liquid of the gas control channels (GC1,GC2) is pushed into the liquid channel (c) while imparting the adequate gas pressure until the gas and liquid interface reaches JC1 or JC2 (d)
Figure 2B:
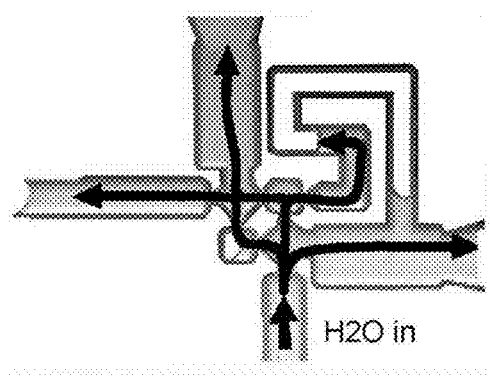
Figure 2C:
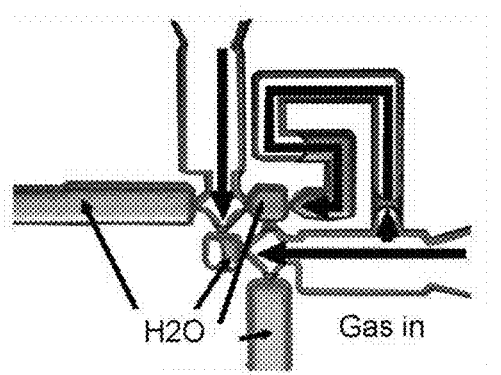
Figure 2D:
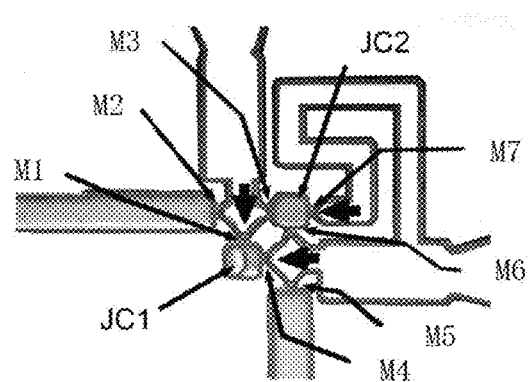

By using the mask shown in FIG. 1*a* to execute the photoetching process, micro-channel systems communicated with each other can be obtained (FIG. 1*b*). The joints between these channels are defined as holes far smaller than the channels themselves. Liquid can flow through the hole but the gas and liquid interface cannot travel through the hole within a certain range of pressure difference due to the force of the surface tension, thereby attaining a function of blocking switches. The hole in the figure is denoted by the letter "M". While the liquid is full as shown the red part in FIG. 1*c*, the liquid occupies the liquid channel, and the gas occupies the gas channel under the preservation of the strong gas pressure. The gas channel is used to control and drive the gas, and the liquid channel is the passage where the fluid travels and where the fluid is driven to generate the press head.

2. Working Principle of the Micro-Pump

Due to the requirement of integration, the design of the micro-valve utilizes the space thoroughly, and the channels are tightly connected. Such a dense design does not affect the normal operation of the pump. FIGS. 2*a*-2*d* show the initialization process before the pump is operated. The advantage of the pump is that the pump does not need to be filled in advance, and liquid (FIG. 2*b*) can be directly poured into the hollow channel system (FIG. 2*a*) of the pump via the inlet channel (input). After imparting the initializing gas pressure, the gas and liquid interface is pushed by the gas pressure (FIG. 2*c*) to the joints of JC1 and JC2 (FIG. 2*d*), thereby fulfilling the initialization of the pump.

Figure 3A:
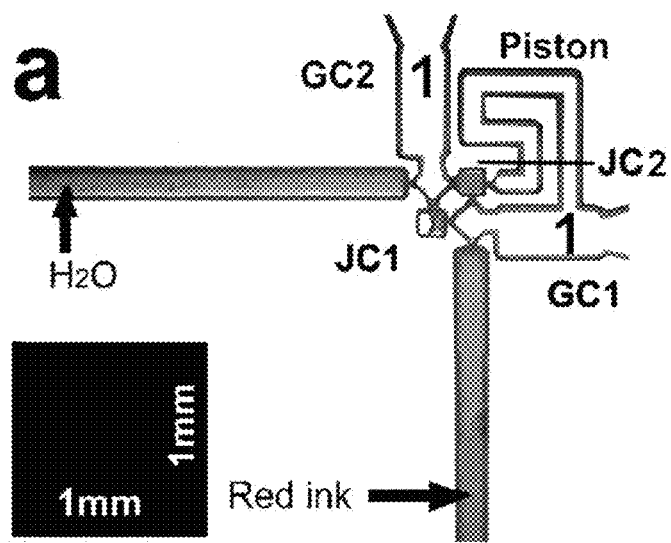
FIGS. 3a-3f are schematic views showing the driving principle on which the pump is based under the digital gas pressure control; the circulation of the pump is driven by the two-channel digital command (yellow numbers in the figure); after the initialization of the pump (a, 0s), a loading process is conducted firstly (b, 1 s, red arrows; c, 3 s), then the liquid enters the piston via JC2, and thence the liquid inside the piston is pushed into the outlet channel (d, 8 s, red arrows; e, 9 s) when 7s pump proceeds the outputting stage; and thereafter back to the initialization stage (f, 13 s)
Figure 3B:
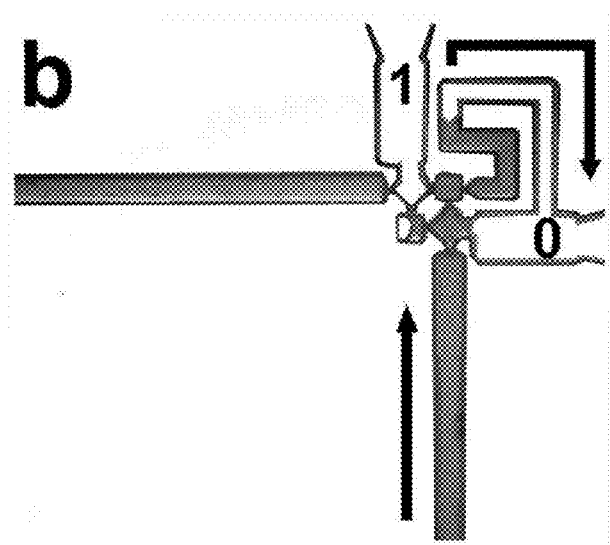
Figure 3C:
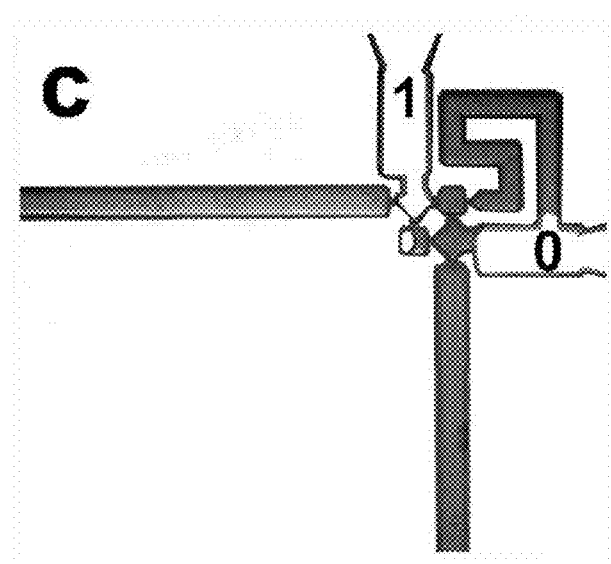
Figure 3D:
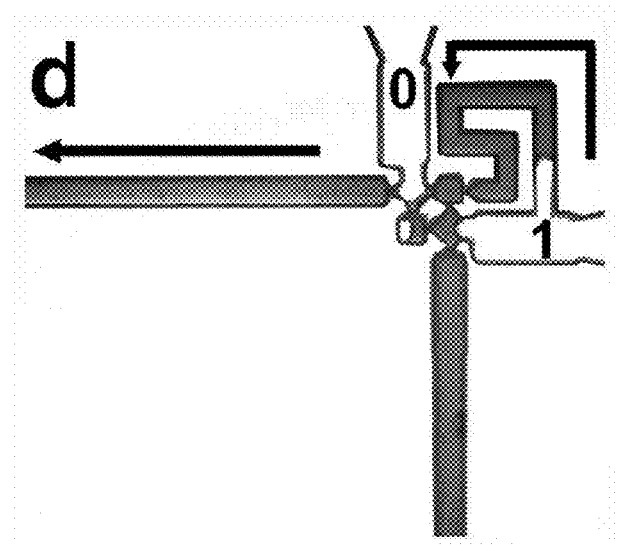
Figure 3E:
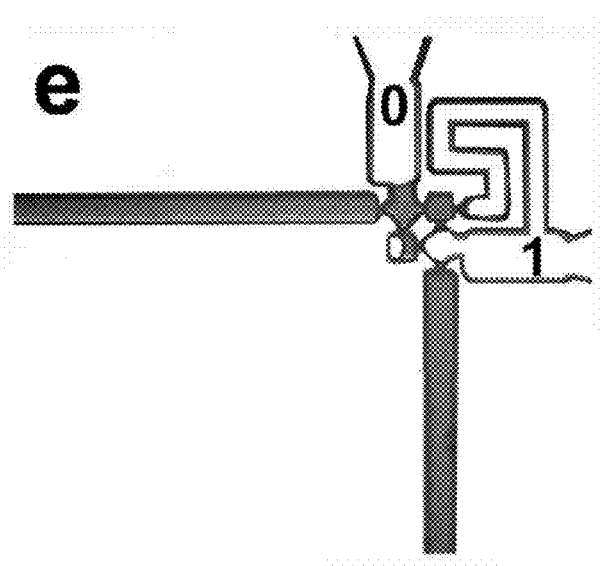
Figure 3F:
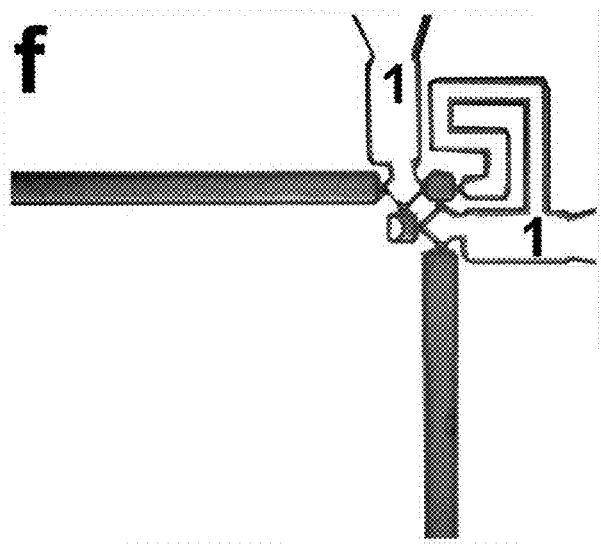

After the initialization, the pump can be driven by a command sequence of a digital gas pressure and operated. First, the initial gas pressure at the two control channels (GC1 and GC2) are set at 1 (1 denotes the high gas pressure, 0 denotes the low gas pressure, shown in FIG. 3*a*). The GC1 is switched to 0 and the valve of GC1 is opened, whereby liquid flows into a piston channel (FIG. 3*b*). When the piston channel is filled with the liquid (FIG. 3*c*), the pressure of GC1 is switched to 1, and the pressure of GC2 is switched to 0, thereby attaining the close state of GC1 valve and the open state of GC2 valve. Accordingly, the liquid in the piston channel can only pass the valve 2 and enter the outlet channel under the gas pressure and cannot go back to the inlet channel (FIG. 3*d*). After the liquid in the piston is all output to the outlet channel (FIG. 3*e*), GC2 is set at 1, and the outlet valve is closed (FIG. 3*f*), thereby becoming the initializing state. Such operation is circulated and repeated to allow the pump to activate and make the liquid in the inlet channel go into the outlet channel. The important part is that the piston channel is much longer than the valve channel, and the completion of the close of the valve of the high pressure chamber is much earlier than the piston driving action, whereby the same high-pressure device can fulfill a dual-function which closes the valve of GC1 firstly and thereafter makes the liquid in the driving piston go into the outlet channel.

3. Performance Test of the Micro-Valve

Figure 4:
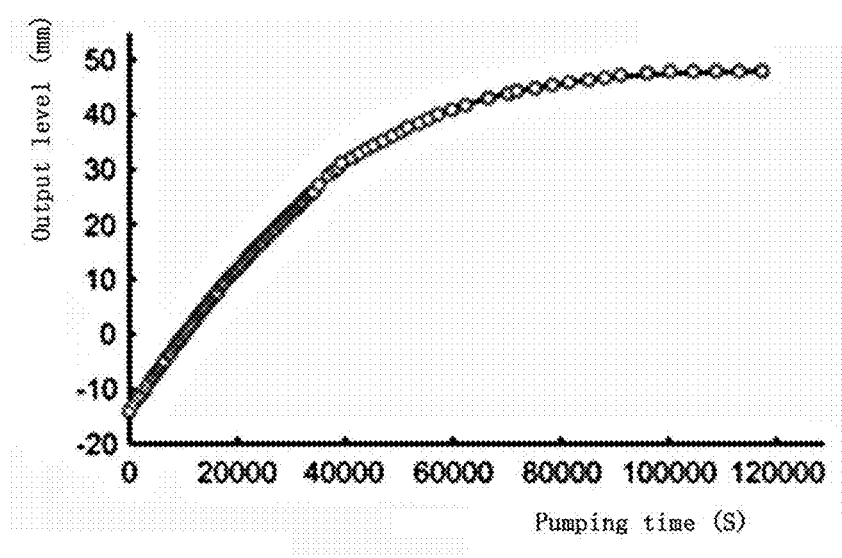
FIG. 4 is a schematic view showing a measurement of the output efficiency of the pump, where the liquid output by the pump enters a vertical tube for being measured.
Figure 5:
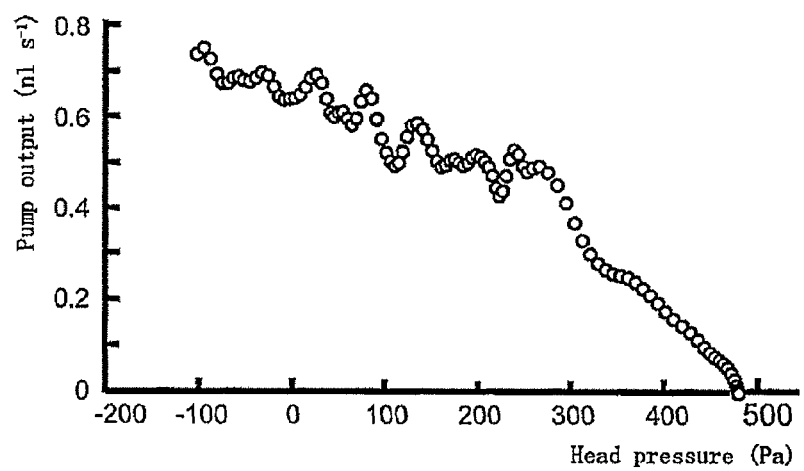
FIG. 5 is a schematic view showing a calculated result of the output of the pump, where the relationship between the output of the pump bulk and the press head is shown.

FIG. 4 shows the output performance of a micro-valve, wherein the pump is able to output the pure water to the height of 40 mm, and the efficiency of the bulk output is measured (FIG. 5). Under the maintenance of bulk output at the velocity of 0.5-0.7 nl/s, the press head can reach to about 300 Pa.

4. Compatibility of Integrating the Micro-Valve and Other Micro-Components

Figure 6:
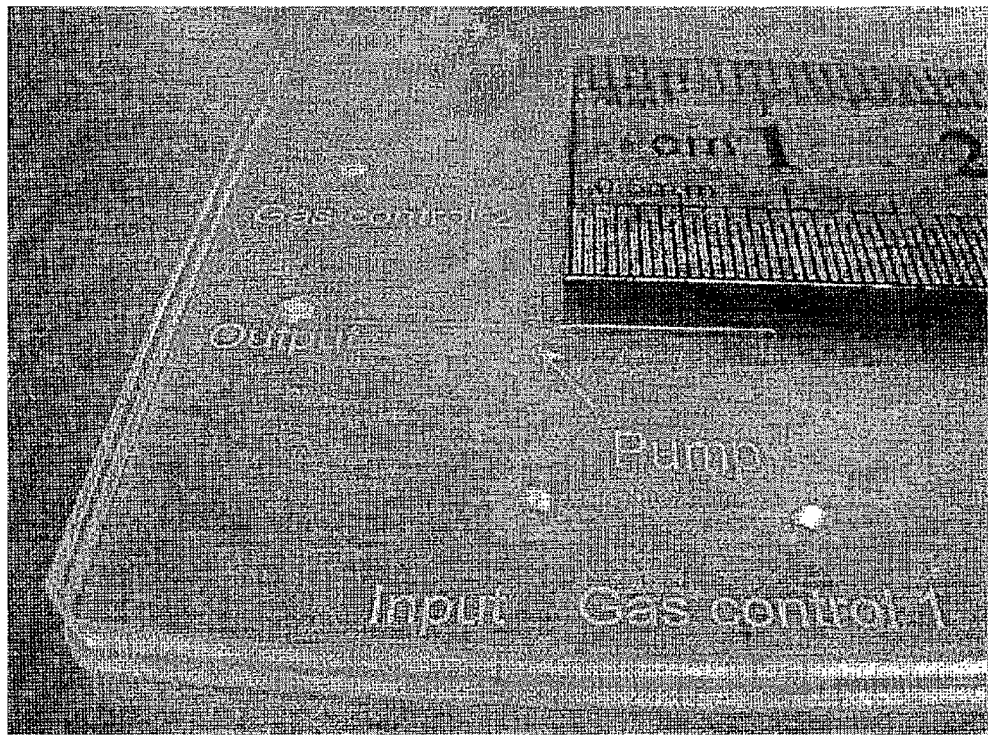
FIG. 6 is a schematic view showing the pump in a real chip.
Figure 7:
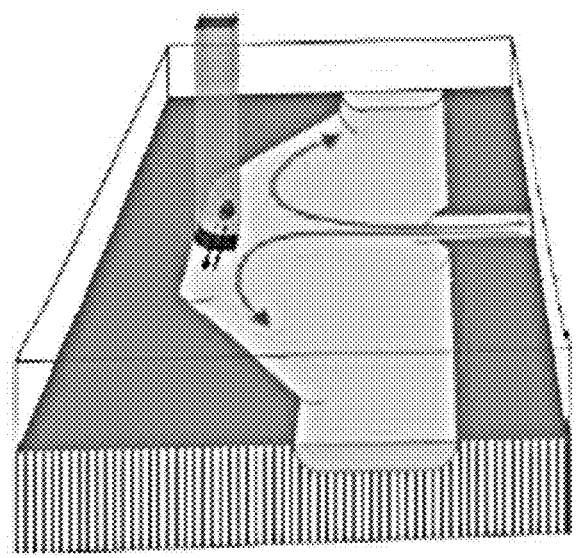
FIG. 7 is a schematic view showing a unicellular chip structure formed by one-time photoetching.
Figure 8:
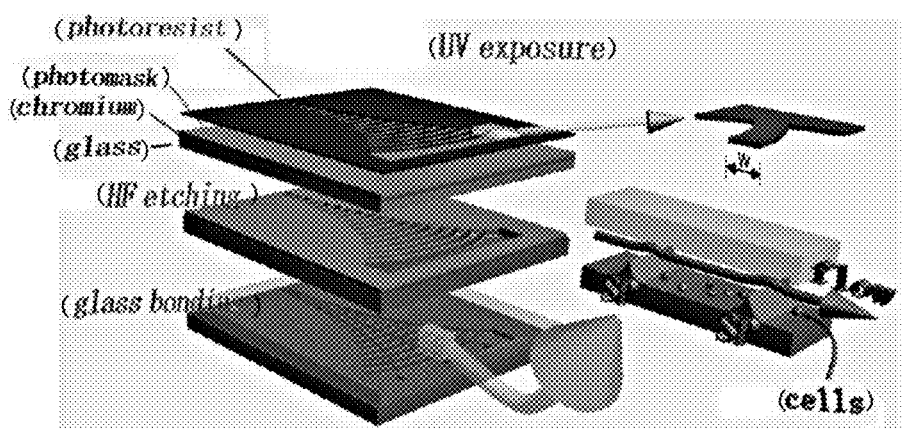
FIG. 8 is a schematic view showing a multicelluar chip structure formed by one-time photoetching.
Figure 9:
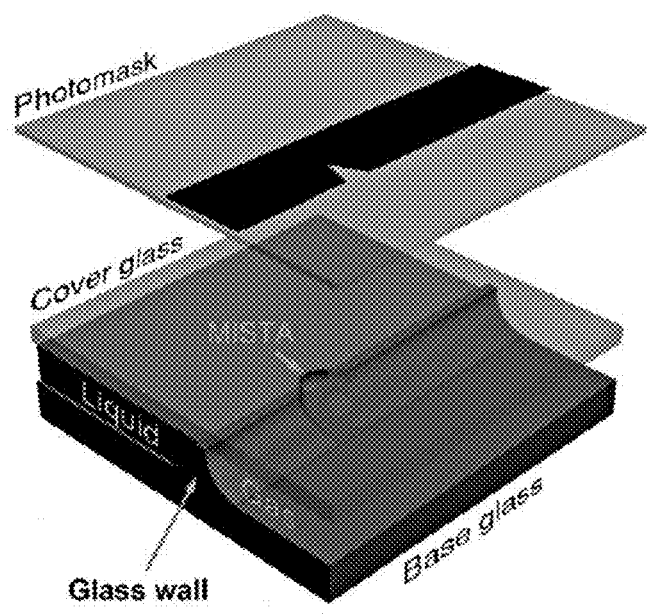
FIG. 9 is a schematic view showing a gas exchange chip structure formed by one-time photoetching.
Figure 10A:
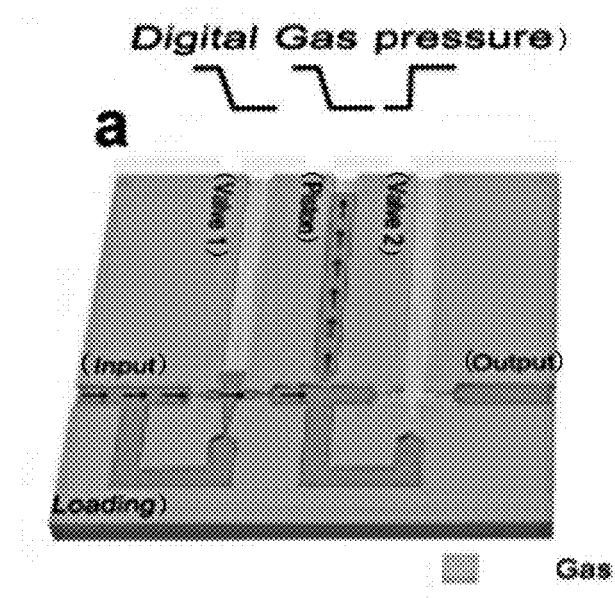
FIGS. 10*a*-10*b* are schematic views showing the chip structure of the valve-piston-valve pump formed by one-time photoetching.
Figure 10B:
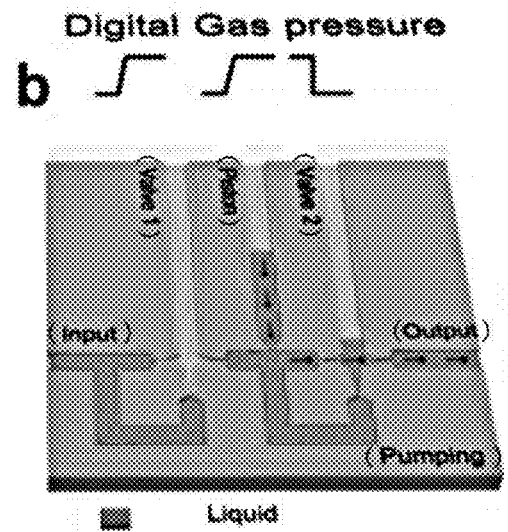

FIG. 6 is an appearance of a glass chip of the micro-valve, wherein the entire structure exists on a planar surface between two glass. Because other micro-components, such as the unicellular experimental unit (FIG. 7), the multicelluar experimental unit (FIG. 8), the gas exchange unit (FIG. 9) and the micro-valve (FIG. 10), can use the same technique and can be made on a same mask, thereby fulfilling the same chip integration having chip micro-components with different functions. The appearance of the made chip is similar to the appearance of FIG. 6, and various structures are able to exist between the two glass.

5. Industrialized Production of the Integrated Chip

Figure 11:
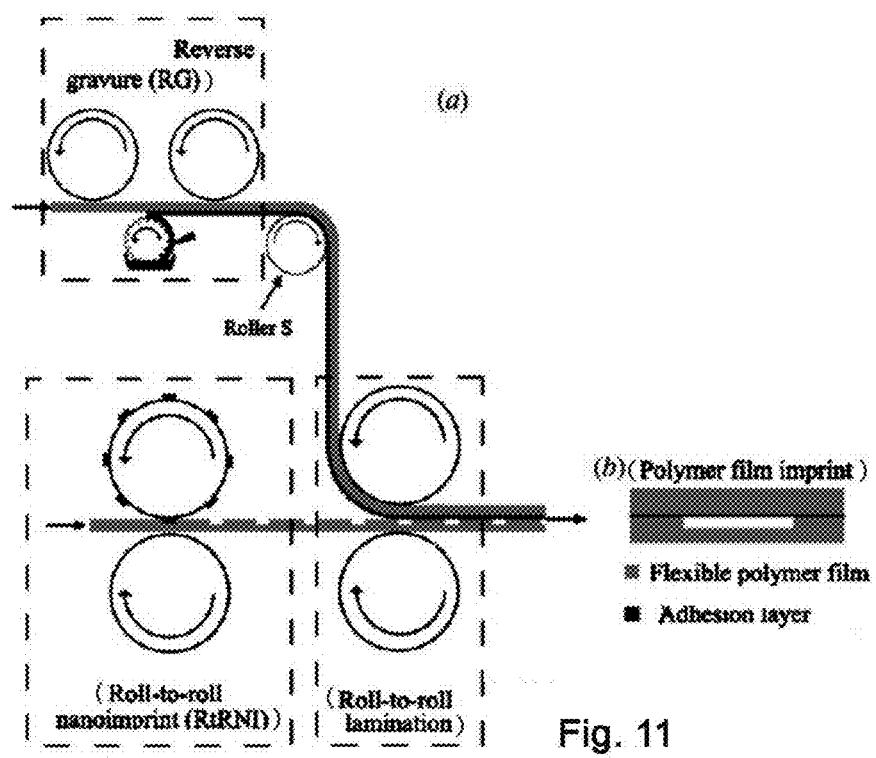
FIG. 11 is a schematic view showing a technique of manufacturing the low-cost chip by printing technique (this figure is cited from Micromech. Microeng. 21 (2011)

Because the space structure of the micro-channels can be rolled by using the rolling sleeve (in a convex-concave design) with a micro-channel pattern (FIG. 11), it especially adapted to the micro-components with the single-layered and simple design. Therefore, the top and bottom glass as shown in FIG. 6 can be replaced by other printable rolled materials, such as plastic materials, thereby executing the industrialized production and manufacturing the chip with very low cost.

6. Multi-Layered Integration Method of the Chip

Figure 12:
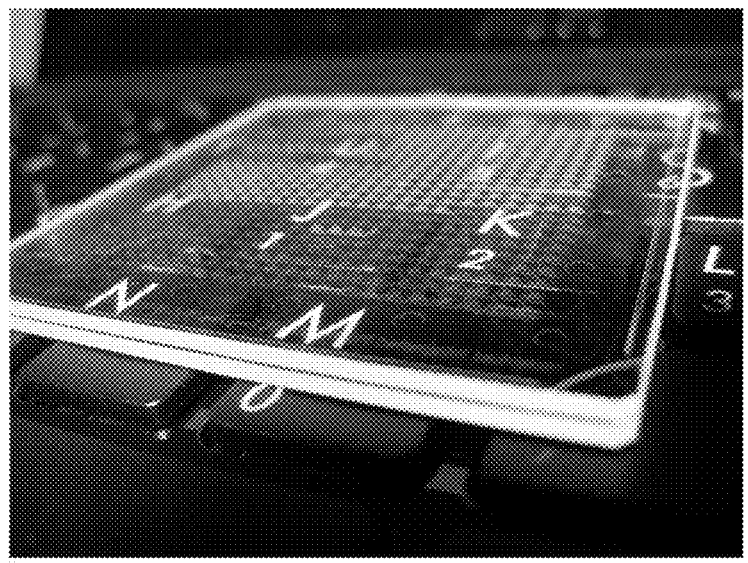
FIG. 12 is a schematic view showing a glass chip integrated into 529 pumps on a glass of 6 cm side length via the one-time etching technique.
Figure 13A:
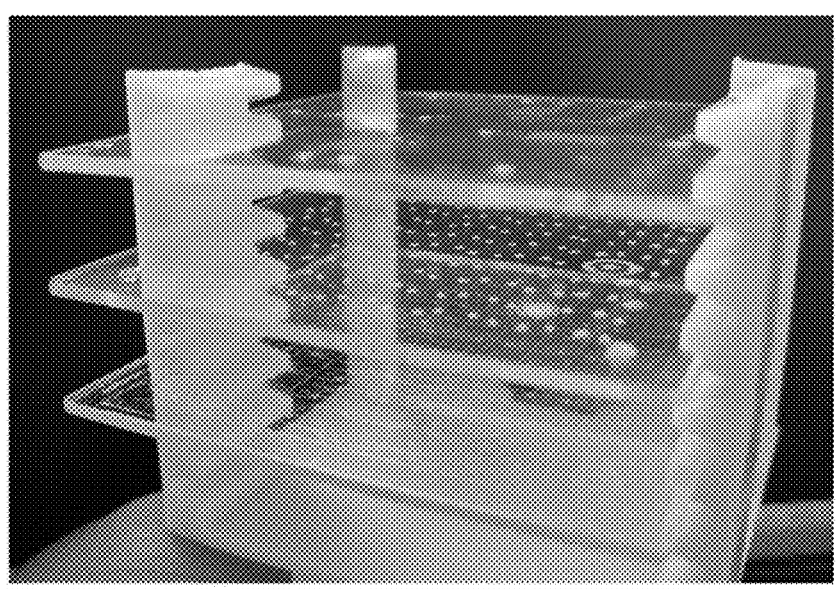
FIGS. 13*a*-13*b* are schematic views showing the integration of the multi-layered chips, where two chips are integrated via the chip with holes.
Figure 13B:
Figure 14:
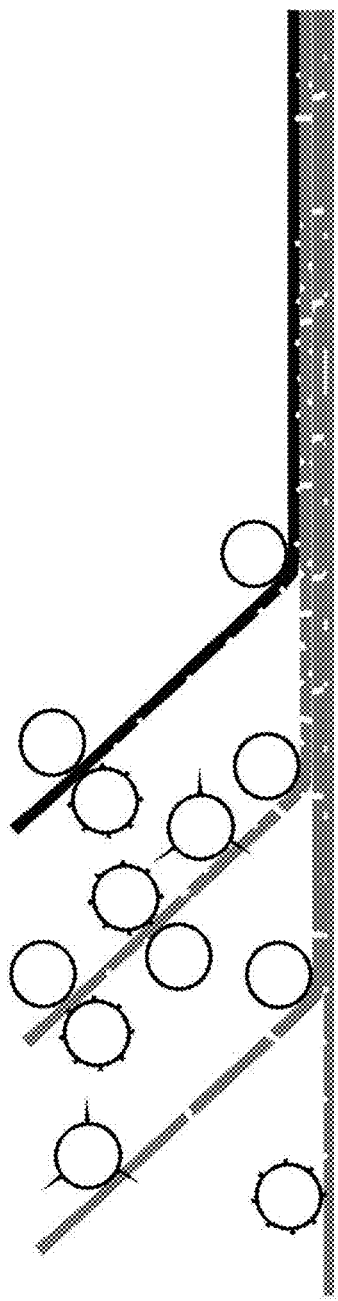
FIG. 14 is a schematic view showing the industrialized production of multi-layered high-integration micro-channel chips.

Taking the space reserved between the pumps into consideration, an interstice of 1 mm can be set between the pumps. Therefore, more than 500 independent micro-valves (FIG. 12) can be integrated on the single-layered planar chip of 50×50 mm (plus a square chip with a margin of 60×60). If a middle layer is utilized to execute the top-bottom communication (FIGS. 13a-13b), the top and bottom micro-channels, which can be gas channel or the liquid channel, are integrated together to become a dual-layered chip structure. By this method, more layers can be superimposed to attain the multi-layered chips to solve the problem of the integration of solid multi-layered chips. As aforesaid, such multi-layered chips can execute a mass production by using the industrial printing method, as shown in FIG. 14.

What is claimed is:

1. A micro-channel chip, integrated as a single layer or multi-layer, comprising
    two gas control channels (GC1, GC2), disposed perpendicular to each other, to control a gas flow each contained therein;
    a liquid inlet channel, disposed perpendicularly without intersecting to GC1,
    a liquid outlet channel, disposed perpendicularly without intersecting to GC2,
    JC1 and JC2, two square micro-channels, disposed respectively in quadrant III and quadrant I in a Cartesian plane, in communication to Valve 1 and Valve 2 disposed respectively in quadrant II and quadrant IV in the Cartesian plane;
    a piston channel, integrated with Valve 1 for the piston channel and Valve 1 to operate under a same signal of gas pressure,
    the piston channel being much longer than each of valve channels of Valve 1 and Valve 2, such that Valve 1 and Valve 2 can be closed at high pressures much earlier than a liquid in the piston channel is driven to the liquid outlet channel, and
    a micro pump, controlled by an ordered loop of digital commands of a 1-by-2 matrix, beginning with (1, 1), followed by (0,1), then by (1,0) and back to (1,1), corresponding respectively to a gas pressure of GC1 and GC2,
    the micro pump, made of any materials, which includes the two micro-valves Valve 1 and Valve 2, which open at a command denoting a low gas pressure, and close at a command denoting a high gas pressure, by deforming under a pressure difference resulting from a surface tension, and Valve 1 and the piston channel being integrated to operate under identical signals of pressure, and
    a plurality of micro-channels, joining each other at a plurality of joints (M's), which are holes of a size substantially smaller than that of the micro-channels as passages for the liquid unless otherwise closing off under the a high pressure difference;
    one of said gas control channels (GC1)
    communicating with one end of said piston channel and communicating with said two micro-valves and said liquid inlet channel respectively via said micro-channels,
    the other one of said gas control channels (GC2)
    communicating with said two micro-valves and said liquid outlet channel respectively via said micro-channels,
    the other end of said piston channel communicating with one of said micro-valves via said micro-channels, wherein
    I) when a liquid inputs to the input channel:
    both GC1 and GC2 are initialized with a high pressure to make Valve 1 and Valve 2 close;
    II) GC1 switched to a low pressure to release Valve 1 to open for the liquid to flow into the piston channel;
    III) when the piston channel is filled with the liquid:
    GC1 switched to a high pressure to close Valve 1, and GC2 switched to a low pressure to release Valve 2 to open, making the liquid to flow from the piston channel to the outlet channel, not to the inlet channel; and
    IV) when the outlet channel is filled with the liquid from the piston channel:
    GC2 switched to a high pressure to close Valve 2.

2. The micro-channel chip according to claim 1, wherein said micro-channels are gradually narrowed.

3. The micro-channel chip according to claim 1, wherein a structure of said micro-valve is disposed within an area of one square millimeter on said chip.

4. The micro-channel chip according to claim 1, wherein said micro-pump is defined as a micro-component, which is driven by imparting digital pressure signals to said two gas control channels.

5. The micro-channel chip according to claim 1, wherein said micro-channel chip and other chip units formed by one-time photoetching are concurrently designed on a mask to be integrated by etching at one time.

* * * * *